United States Patent
Hasegawa

(10) Patent No.: US 10,094,786 B2
(45) Date of Patent: Oct. 9, 2018

(54) OPTICAL DISTANCE SENSOR

(71) Applicant: DENSO WAVE INCORPORATED, Chita-gun, Aichi-pref. (JP)

(72) Inventor: Yuki Hasegawa, Chita (JP)

(73) Assignee: DENSO WAVE INCORPORATED, Aichi-pref. (JP)

(*) Notice: Subject to any disclaimer, the term of this patent is extended or adjusted under 35 U.S.C. 154(b) by 323 days.

(21) Appl. No.: 15/066,644

(22) Filed: Mar. 10, 2016

(65) Prior Publication Data
US 2016/0274035 A1    Sep. 22, 2016

(30) Foreign Application Priority Data

Mar. 17, 2015 (JP) .................................. 2015-053410

(51) Int. Cl.
| | |
|---|---|
| *G01C 3/08* | (2006.01) |
| *G01N 21/94* | (2006.01) |
| *G01N 21/88* | (2006.01) |
| *G01S 17/10* | (2006.01) |
| *G01S 17/42* | (2006.01) |
| *G01S 7/481* | (2006.01) |
| *G01S 7/497* | (2006.01) |

(52) U.S. Cl.
CPC .......... *G01N 21/94* (2013.01); *G01N 21/8851* (2013.01); *G01S 7/481* (2013.01); *G01S 7/497* (2013.01); *G01S 17/10* (2013.01); *G01S 17/42* (2013.01); *G01N 2201/06113* (2013.01); *G01S 7/4812* (2013.01); *G01S 2007/4975* (2013.01)

(58) Field of Classification Search
CPC combination set(s) only.
See application file for complete search history.

(56) References Cited

U.S. PATENT DOCUMENTS

2009/0015824 A1 * 1/2009 Shubinsky ............. G01N 21/94
356/237.3

FOREIGN PATENT DOCUMENTS

JP    H10-90412 A    4/1998

* cited by examiner

*Primary Examiner* — Samantha K Abraham
(74) *Attorney, Agent, or Firm* — Oliff PLC

(57) ABSTRACT

An optical distance sensor includes a foreign matter detector that utilizes a coaxial optical system for distance measurement as well as utilizing a first pulse and a second pulse respectively caused as an internal reflection of a front screen and as a reflection from a detection object for a detection of foreign matter deposit on the front screen based on a difference of light amounts between the first and second pulse. The foreign matter detector determines that the optical distance sensor is in a normal state, in an obstacle cover state or in a foreign matter deposit state respectively corresponding to three states of the front screen (i.e., (i) having no foreign matter deposit, (ii) having a covering obstacle, or (iii) having a foreign matter deposit).

8 Claims, 6 Drawing Sheets

OPTICAL DISTANCE SENSOR

CROSS REFERENCE TO RELATED APPLICATION

The present application is based on and claims the benefit of priority of Japanese Patent Application No. 2015-53410, filed on Mar. 17, 2015, the disclosure of which is incorporated herein by reference.

TECHNICAL FIELD

The present disclosure generally relates to an optical distance sensor.

BACKGROUND INFORMATION

An optical distance sensor has a light emitter for emitting a light and a light receiver for receiving the light, in which the light emitted from the emitter reaches the receiver after a reflection on a detection object. In some cases, such a distance sensor has a coaxial optical system that puts the emitter and the receiver on the same optical axis.

In case that the optical distance sensor having the coaxial optical system, the light (e.g., a laser beam or the like) emitted from the emitter passes through a front screen disposed at a front part of the sensor, and is projected toward an outside of the sensor. The light reflected by the outside object of the sensor passes through the front screen again, and enters into the light receiver.

Thus, in case that the optical distance sensor has the coaxial optical system, the light emitted from the emitter passes through the front screen, and is emitted toward the outside of the sensor. Therefore, a part of the emitted light is reflected by an inner surface of the front screen as an internal reflection. The light reflected by the inner surface of the front screen enters into the light receiver separately from the light reflected by the outside object. That is, the light caused by the internal reflection results in a false sensing in the measurement of the distance by the optical distance sensor (i.e., the internal reflection by the front screen). Thus it is desired to reduce the internal reflection as much as possible.

Further, as for an external surface of the front screen, foreign matter such as rain, soil and the like are easily deposited. When foreign matter (e.g., dirt, soil and the like) deposit on the front screen, the light emitted from the emitter is reflected by the deposited foreign matter. Therefore, when the foreign matter deposits on the front screen, the measurement accuracy of the distance to the outside object deteriorates, similar to the case when the internal reflection is caused on the inner surface of the front screen.

Thus, by disposing a triangular prism-like projecting object on the case equivalent to the front screen, and by emitting the laser light from a dirt-detection light emitter to the projecting object, the dirt is detected in a conventional sensor, (e.g., a sensor disclosed in a patent document, JP H10-090412 A (patent document 1)).

However, the sensor in the patent document 1 can detect the dirt only on a part of the case (i.e., at a position of the projecting object). Further, the sensor in the patent document 1 is required to have a separate optical system only for the detection of the dirt. Thus, the number of components is increased, and the structure of the sensor becomes complicated in the conventional sensor.

SUMMARY

It is an object of the present disclosure to provide an optical distance sensor that is capable of detecting the foreign matter deposited at any position on an entire surface of the front screen with sufficient accuracy, without having additional components, and without complicating a sensor structure (i.e., solely by using the optical system for the distance measurement).

In an aspect of the present disclosure, an optical distance sensor includes an optical system having a coaxial optical path on which a light emitter for emitting light that is reflected by a detection object, and a light receiver for receiving a reflected light are coaxially placed, together with a front screen placed on the coaxial optical path. The optical distance sensor includes a time counter counting time between emission of the light from the light emitter and reception of the light by the light receiver as counted time, and an foreign matter (FM) detector detecting a deposition of foreign matter on the front screen based on a relationship between the counted time and an amount of the light received by the light receiver.

The FM detector detects a first pulse as the light not passing through the front screen and a second pulse as the light reflected back from the detection object. Here, the FM detector determines that (i) a first light amount L1 of the first pulse is an internal reflection amount Li of the light reflected by an inner surface of the front screen, and (ii) the front screen is in a normal state without foreign matter deposited on the front screen, when a second light amount L2 of the second pulse is greater than the first light amount L1 of the first pulse.

Also, the FM detector determines an obstacle cover state that the front screen is covered by an obstacle that is wider than the front cover, when the first light amount L1 of the first pulse is detected to be substantially equal to an excess light amount Lo, without detection of the second pulse.

Further, the FM detector determines a foreign matter deposit state of having foreign matter on an outside of the front screen, when (i) the first light amount L1 of the light of the first pulse is greater than the internal reflection light amount Li and is smaller than the excess light amount Lo, and (ii) the second light amount L2 of the second pulse is smaller than the second light amount L2 detected during the normal state.

Thus, the foreign matter detector detects the foreign matter deposited on the front screen, based on a difference of light amounts between the first pulse corresponding to the internal reflection and the second pulse corresponding to reflection by the outside object, taking advantage of the coaxial optical system for distance measurement.

That is, the optical distance sensor of the present disclosure positively utilizes the internal reflection otherwise shunned for its negative effects for the detection of the foreign matter on the front screen.

Therefore, the foreign matter deposited on the front screen can be detected with sufficient accuracy over the whole surface of the screen, without adding extra parts and complication of the sensor structure.

Further, the light emitter emits the light for each of scan areas that are positioned between a scan start position and a scan end position at constant intervals. Also, in the foreign matter deposit state, the FM detector detects an angle of the foreign matter deposition based on a range of the scan areas from which the light receiver receives the first pulse having (i) a lower limit amount (La) that is set for noise filtering and (ii) a pulse width greater than a determination value $\beta$.

Here, the foreign matter detector detects not only the position where the foreign matter is deposited, but also the range of the scan areas having the foreign matter (i.e., the size of the foreign matter).

The optical distance sensor may have different foreign matter tolerances depending on an installation condition or the like (i.e., extent to which the foreign matter is allowed to deposit on the sensor may vary). When the range of the foreign matter deposit on the front screen is detected as described above, whether such deposit is allowable or not is determined. Therefore, the foreign matter detection is performed with high accuracy according to the condition of the foreign matter.

Further, the FM detector determines that the foreign matter deposition exists on the front screen, when a ratio A of the scan areas in the foreign matter deposit state against an entire range of the scan areas is equal to or greater than a preset ratio γ continuously for a first preset time T1. Also, after a determination of deposition of the foreign matter on the front screen, the FM detector determines that the front screen is without foreign matter deposition, when the ratio A of the scan areas in the foreign matter deposit state against the entire range of the scan areas is equal to or smaller than a preset ratio continuously for a second preset time T2.

Therefore, accurate detection of the foreign matter is performed according to the use environment of the sensor.

Further, the foreign matter detector determines the amount of the received light by the light receiver based on an intensity of the received light. The light receiver outputs an electrical signal such as a voltage according to the intensity of the received light. The foreign matter detector uses the output of the electrical signal according to the intensity of the received light as the amount of the received light as it is (i.e., without change). Therefore, the amount of the received light is converted to a simple magnitude of the signal value, thereby simplifying an internal processing of the optical distance sensor. That is, even when the resolution of the scanning is high, the internal processing is quickly performable.

Further, the foreign matter detector determines a timewise pulse width of the first and second pulses of the light received by the light receiver as the amount of the received light. When the reflected light becomes stronger, the width of the pulse of the electrical signal output from the light receiver increases. That is, a timewise amount between a pulse start time and a pulse stop time increases when the reflected light gets stronger. The foreign matter detector uses such a timewise amount (i.e., width of the pulse, as the amount of the received light). Thereby, the amount of the received light is converted to a time between a signal ON and a signal OFF, thereby simplifying the internal processing. That is, even when the resolution of the scanning is high, the internal processing is quickly performable.

Further, the foreign matter detector determines an energy of the light received by the light receiver as the amount of the received light. The energy of the received light means an integration value of the first pulse or the second pulse. In other words, the energy of the light is calculated as a time-integration of the first/second pulse based on the output of the electrical signal according to the intensity of the received light by the light receiver. In such manner, the amount of the received light is converted to a simple magnitude of integration value. When the integration values are calculated, even though the calculation time increases, the measurement/calculation accuracy of the amount of the received light is improved, thereby enabling an accurate detection of the foreign matter.

The above summary of the disclosure does not limit the present disclosure to any particular aspect. Rather, the details of the disclosure will be described below.

BRIEF DESCRIPTION OF THE DRAWINGS

Objects, features, and advantages of the present disclosure will become more apparent from the following detailed description made with reference to the accompanying drawings, in which.

DETAILED DESCRIPTION

Hereafter, an optical distance sensor in one embodiment of the present disclosure is described based on the drawings.

Figure 2:
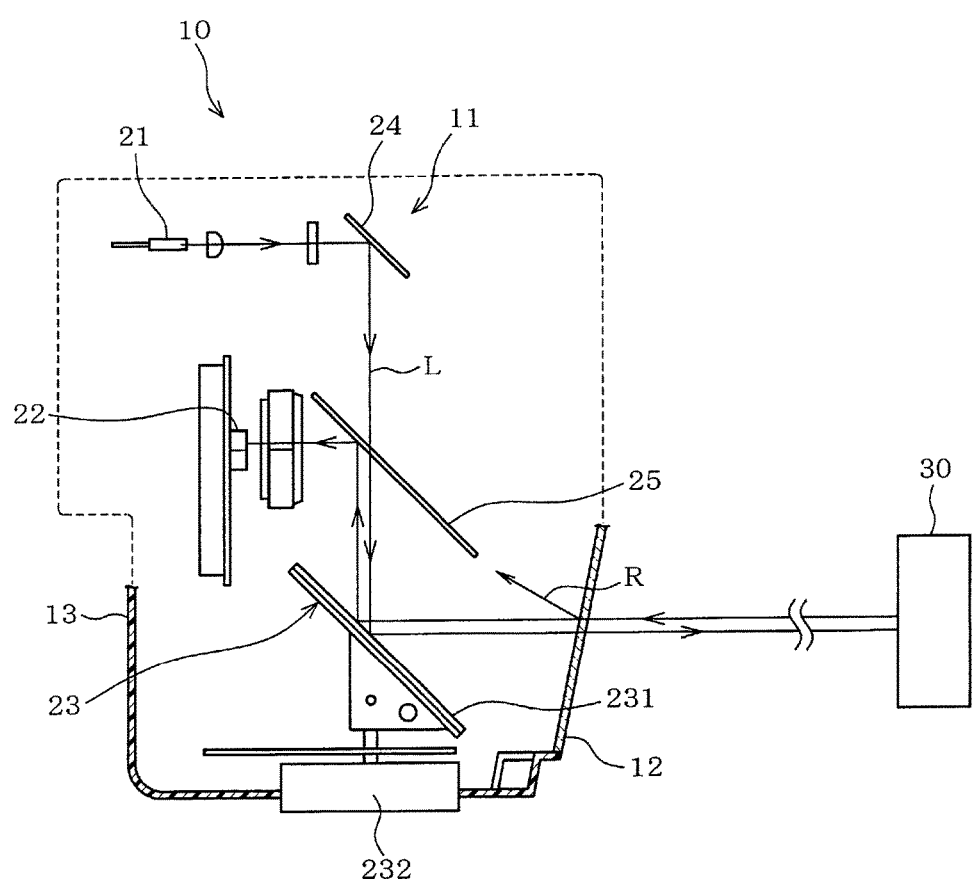
FIG. 2 is an optical configuration diagram of the optical distance sensor in the one embodiment of the present disclosure.

First, a configuration of an optical distance sensor 10 is described. As shown in FIG. 2, the optical distance sensor 10 is provided with an optical system 11, a front screen 12, and a case 13.

Figure 3:
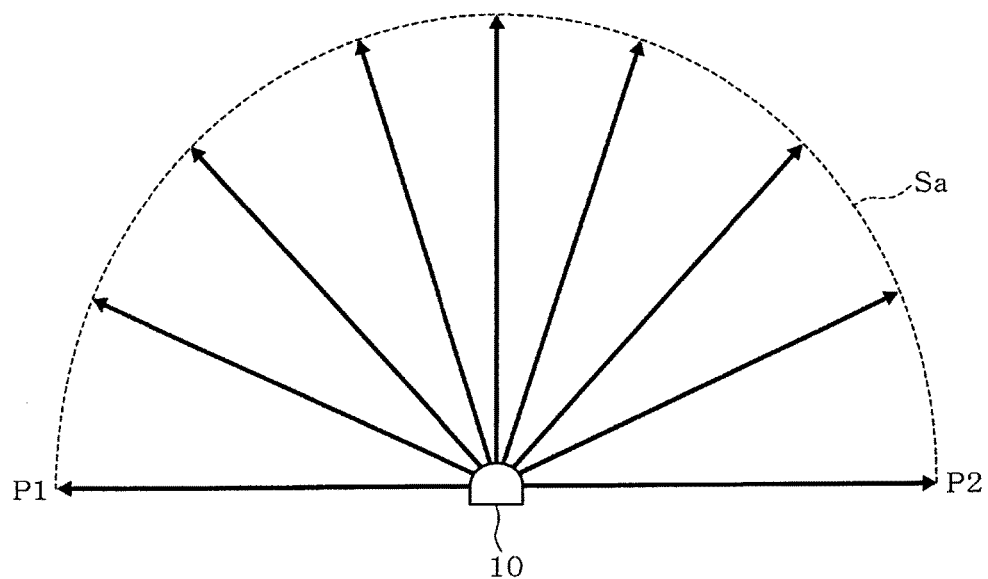
FIG. 3 is an illustration diagram of a scan range of the optical distance sensor in the one embodiment of the present disclosure.

The optical system 11 has a light emitter 21, a light receiver 22, a rotary mirror 23, a turnover mirror 24, and a turnover mirror 25. The light emitter 21 emits a laser beam. The light receiver 22 receives the light that is emitted from the emitter 21 and reflected by a detection object 30. The rotary mirror 23 has a mirror body 231 and a driver 232. The driver 232 rotatably drives the mirror body 231. Thereby, the light from the emitter 21 is emitted by reflecting on the rotary mirror 23 to scan areas set up with equal (i.e., constant) angle intervals from a scan start position P1 to a scan end position P2 as shown in FIG. 3. In the present embodiment, a scan surface Sa that extends in parallel with a ground surface is set up by an angle of about 180 degrees between the scan start position P1 and the scan end position P2. The light from the emitter 21 is thus emitted to each of the scan areas dividing a scan range on the scan surface Sa between the position P1 and the position P2, by the rotation of the mirror 23 within such scan range.

The light emitted from the emitter 21 is turned to the rotary mirror 23 by the turnover mirror 24 shown in FIG. 2. Further, the turnover mirror 25 turns the light from the external detection object 30 and reflected by the rotary mirror 23 to the receiver 22.

The turnover mirror 25 is a half mirror, which passes the light emitted from the emitter 21 and reflected by the mirror 24 to the rotary mirror 23 while reflecting the reflected light reflected by the detection object 30 and reflected again by the rotary mirror 23 toward the mirror 25. Thereby, the laser beam emitted from the emitter 21 is emitted to the external detection object 30 after reflection by the turnover mirror 24 and by the rotary mirror 23. The reflected light reflected by the detection object 30 is then reflected by the rotary mirror 23 and by the turnover mirror 25 to enter into the receiver 22. As a result, the light forms an optical path of L shape, from the emitter 21, to the turnover mirror 24, the rotary mirror 23, the detection object 30, the rotary mirror 23, the turnover mirror 25, and to the receiver 22. Thus, in the present embodiment, the emitter 21 emitting the light and the receiver 22 receiving the light are positioned on the same optical axis. That is, the optical system 11 of the present embodiment constitutes a so-called coaxial optical path.

The front screen 12 and the case 13 form a casing that accommodates the components of the optical distance sensor 10. The front screen 12 is positioned at a waypoint on a coaxial optical path L of the optical system 11. The front screen 12 is made with a transparent material, allowing passage of the light through the front screen 12. Thus, the light emitted from the emitter 21 to the detection object 30 passes through the front screen 12, and the light reflected by the detection object 30 enters into the receiver 22 after passing through the front screen 12.

Figure 1:
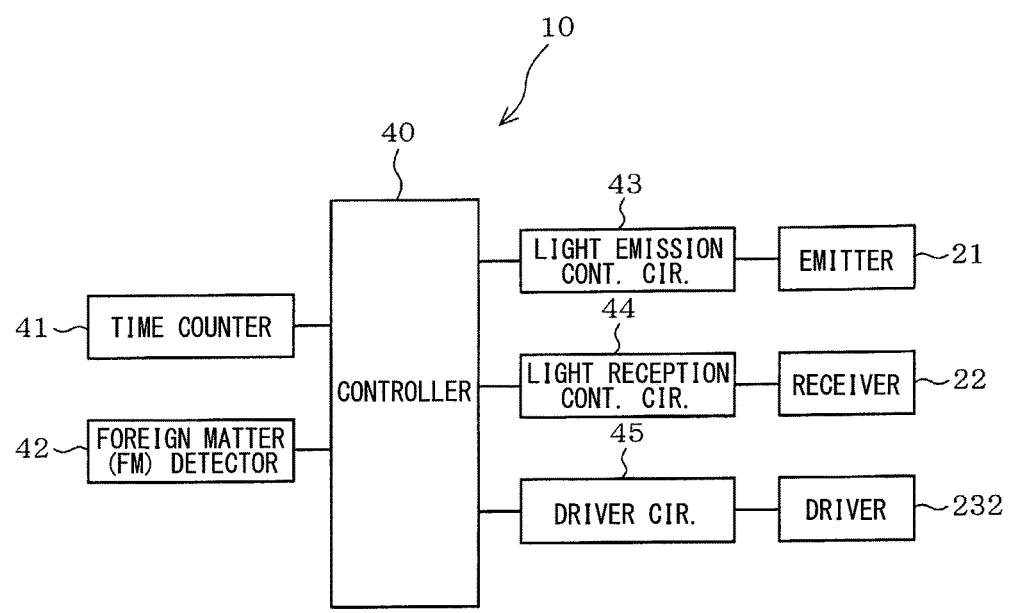
FIG. 1 a block diagram of an optical distance sensor in one embodiment of the present disclosure.

Next, the electrical configuration of the optical distance sensor 10 is described based on FIG. 1.

The optical distance sensor 10 is provided with a controller 40, a time counter 41, and a foreign matter detector 42 (i.e., a FM detector 42). The controller 40 is implemented as a microcomputer 1 which has Central Processing Unit (CPU), Read-Only Memory (ROM), and Random-Access Memory (RAM). The controller 40 controls the entire optical distance sensor 10 by executing a program memorized in ROM with CPU. The optical distance sensor 10 may include a storage medium etc. (not illustrated). The storage medium may be ROM and RAM of the controller 40, which may be used in a shared manner.

The controller 40 is electrically connected with the emitter 21 via a light emission control circuit 43. The controller 40 is also electrically connected with the receiver 22 via a light reception control circuit 44. Further, the controller 40 is electrically connected with the driver 232 of the rotary mirror 23 via a driver circuit 45. Thereby, the controller 40 controls the laser beam emission from the emitter 2, controls the light reception by the receiver 22, and controls the drive of the rotary mirror 23.

The controller 40 realizes the time counter 41 and the foreign matter detector 42 as software modules (i.e., by executing the computer program). The time counter 41 and the foreign matter detector 42 may also be realized as hardware modules, or may also be realized as software-hardware combinations.

The time counter 41 performs time measurement (i.e., measures a lapse time between the emission of the light from the emitter 21 and the reception of the light by the receiver 22). That is, when the light is emitted from the emitter 21 at a time of zero, the time of reception of the reflected light from the detection object 30 may change according to a distance to the object 30. The lapse time measured or counted by the time counter 41 is a time between the emission from the emitter 21 and the reception by the receiver 22.

The foreign matter detector 42 detects whether foreign matter deposits on the front screen 12, based on a relationship between the counted time counted by the time counter 41, and the amount of the received light received by the receiver 22.

Figure 4:
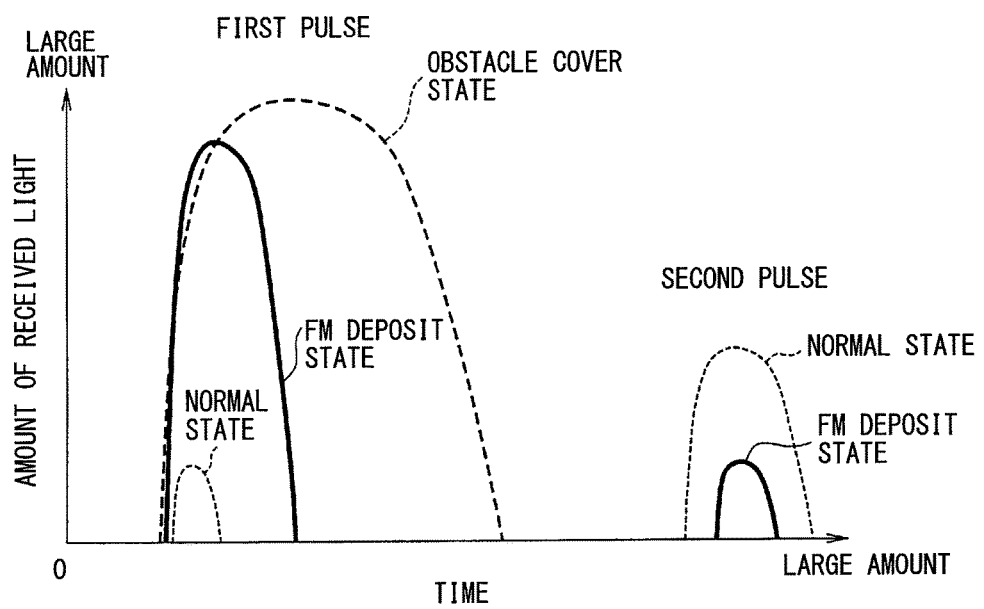
FIG. 4 is an illustration diagram of a relationship between time and an amount of received light in the optical distance sensor in the one embodiment of the present disclosure.

Specifically, the foreign matter detector 42 detects a first pulse and a second pulse, as shown in FIG. 4, from the lapse time counted by the time counter 41, and the amount of the received light by the receiver 22.

As shown in FIG. 2, when passing through the front screen 12, the light emitted from the emitter 21 is partially reflected by the front screen 12 as an internal reflection R. That is, the light emitted from the emitter 21 passes through the front screen 12 by large (i.e., for the most part), but a part of the light from the emitter 21 is reflected thereby (i.e., not passing through the screen 12), to be reflected as the internal reflection R. The internal reflection R serves as the first pulse, and enters into the receiver 22 only in a short time after the emission from the emitter 21. The light passing through the front screen 12 comes back from the external detection object 30 when not obstructed by an obstacle, and enters into the receiver 22. The reflected light from the detection object 30 serves as the second pulse, and enters into the receiver 22 after the first pulse. The foreign matter detector 42 detects whether foreign matter deposits on the front screen 12 based on such characteristics of the first pulse and the second pulse.

In the present embodiment, the amount of the received light is a light intensity, which is an intensity of the received light by the receiver 22 either as the first pulse or the second pulse. The receiver 22 outputs an electrical signal according to the light intensity of the received light. The receiver 22 outputs the electrical signal of high voltage, when the received light is strong, for example, and, when the received light is weak, the receiver 22 outputs the electrical signal of low voltage. The controller 40 obtains the size of the electrical signal outputted from the receiver 22 as the amount of the received light.

(Normal State)

Figure 5:
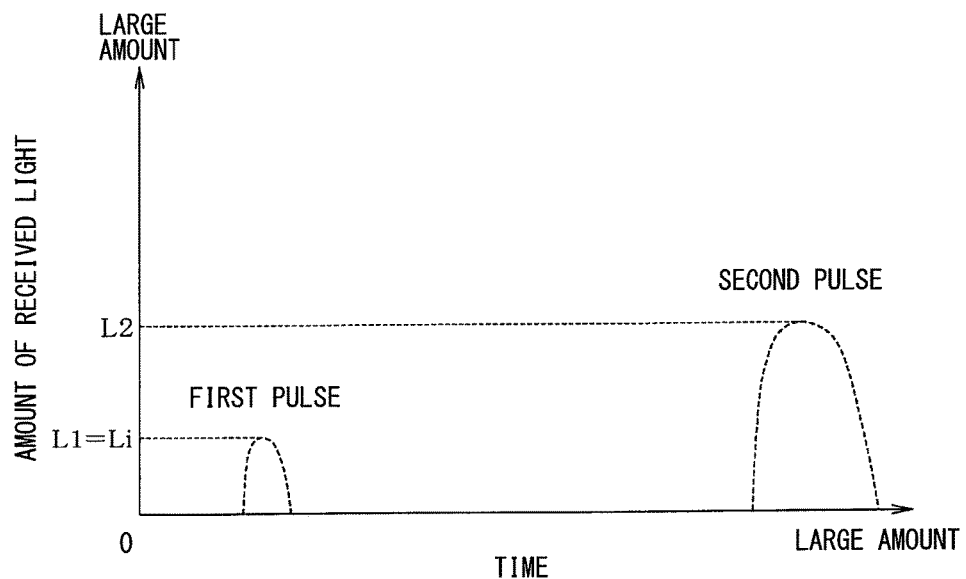
FIG. 5 is an illustration diagram of a relationship between time and an amount of the received light in a normal state in the one of the present disclosure.

When no foreign matter deposits on the front screen 12, the first pulse is generated only by the internal reflection of the front screen 12. Therefore, a detected first light amount L1 of the first pulse takes a small value corresponding to (i.e., substantially equal to) the internal light amount Li of the internal reflection R, as shown in FIG. 5. Thereby, most of the light from the emitter 21 is emitted to the external detection object 30, and is reflected by the external detection object 30. Therefore, a detected second light amount L2 of the second pulse corresponding to the light reflected by the external detection object 30 becomes greater than the first light amount L1 of the first pulse.

Thus, when no foreign matter deposits on the front screen 12, the second light amount L2 becomes greater than the first light amount L1. Then, it is determined by the foreign matter detector 42 that the optical distance sensor 10 is in a normal state in which no foreign matter deposits on the front screen 12 (i.e., the front screen 12 is without foreign matter deposits), when the second light amount L2 is greater than the first light amount L1.

The foreign matter detector 42 sets the first light amount L1 of the first pulse, as an internal light amount Li of the internal reflection R in the normal state.

(Obstacle Cover State)

Figure 6:
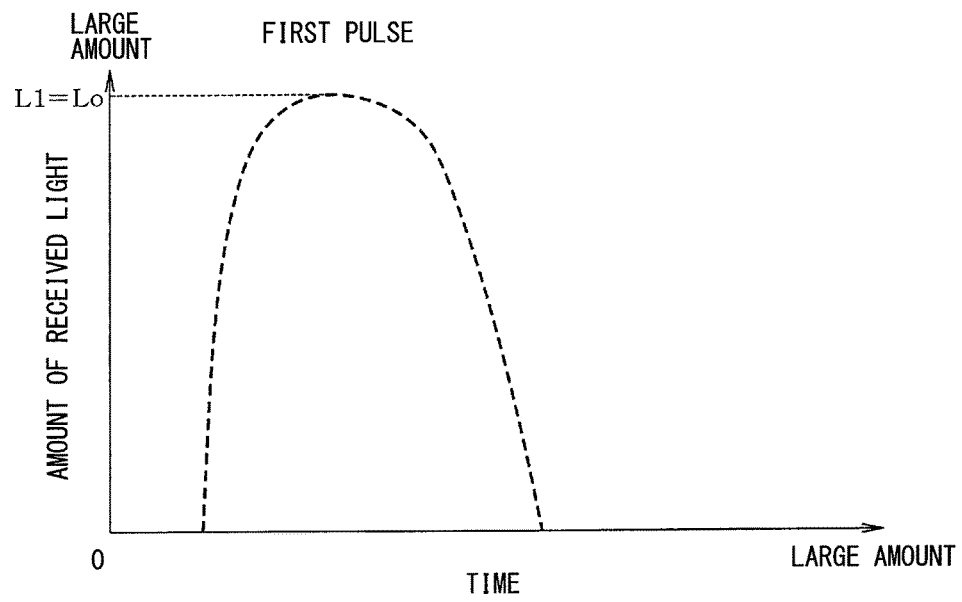
FIG. 6 is an illustration diagram of a relationship between time and an amount of the received light in an obstacle cover state in the one of the present disclosure.

When the front screen 12 is covered by an obstacle (i.e., when there is a large obstacle so close to the front screen 12 that the screen 12 is substantially covered by such obstacle), the detected first light amount L1 of the first pulse becomes very large, as shown in FIG. 6. Further, when the obstacle substantially covers the front screen 12, the light emitted from the emitter 21 does not reach the detection object 30; if the light ever does reach the object 30, the reflected light from the object 30 cannot come back to enter into the receiver 22. Therefore, when the front screen 12 is in an obstacle cover state, the second pulse is not detected (i.e., without detection of the second pulse). If the light is ever detected, the second pulse is very small.

Therefore, when the foreign matter detector 42 detects a light amount L1 substantially equal to an excess light amount Lo that is greater than the first light amount L1 that corresponds to the internal light amount Li of the internal reflection R of the first pulse detected during the normal state, and does not detect the second pulse or detects the second pulse only in a small amount, it is determined that the optical distance sensor 10 is in the obstacle cover state. In the obstacle cover state, the front screen 12 (i.e., an outside surface of the screen 12) is covered mostly, or substantially entirely with fallen leaves, dust, etc., for example.

(Foreign Matter (FM) Deposit State)

Figure 7:
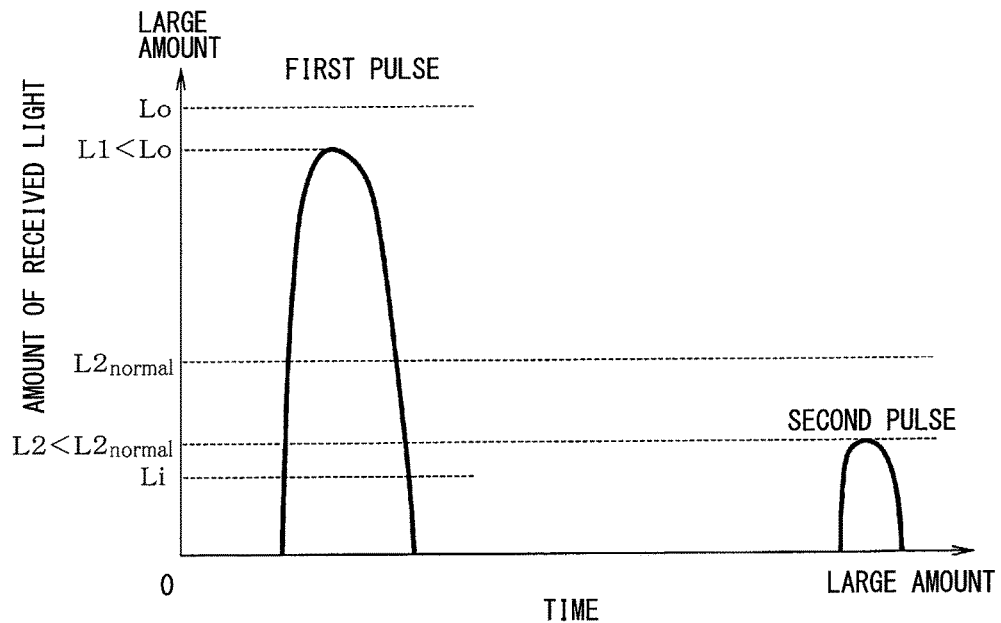
FIG. 7 is an illustration diagram of a relationship between time and an amount of the received light in a foreign matter deposit state in the one of the present disclosure.

When foreign matter deposits on the front screen 12, which is relatively small as compared with the obstacle, a part of the light emitted from the emitter 21 is reflected by the foreign matter on the screen 12, and the rest of the light from the emitter 21 is reflected by the external detection object 30. Therefore, when the foreign matter deposits on the front screen 12, as shown in FIG. 7, the first pulse and the second pulse are detected. In such a situation, the light emitted from the emitter 21 and reaching the external detection object 30 is weakened by the foreign matter deposited on the front screen 12. Therefore, the amount of the received light in the second pulse becomes smaller as compared with the second light amount L2 of the second pulse in the normal state.

Thus, when (i) the first light amount L1 in the first pulse is greater than the internal light amount Li, and is smaller than the excess light amount Lo and (ii) the amount of the received light in the second pulse is smaller than the second light amount L2 in the normal state, the foreign matter detector 42 determines that the optical distance sensor 10 is in a foreign matter (FM) deposit state.

(Foreign Matter Deposit Area Detection)

The foreign matter detector 42 detects an angle of the foreign matter deposited on the front screen 12 (i.e., a deposit range of the foreign matter), when it is determined that the sensor 10 is in the foreign matter deposit state.

As mentioned above, the emitter 21 emits the laser beam for every scan area set up with equal angle intervals from the scan start position P1 to the scan end position P2. The foreign matter detector 42 detects the foreign matter deposit range based on the foreign matter detected as deposited on the front screen 12 between the scan start position P1 and the scan end position P2.

Figure 8:
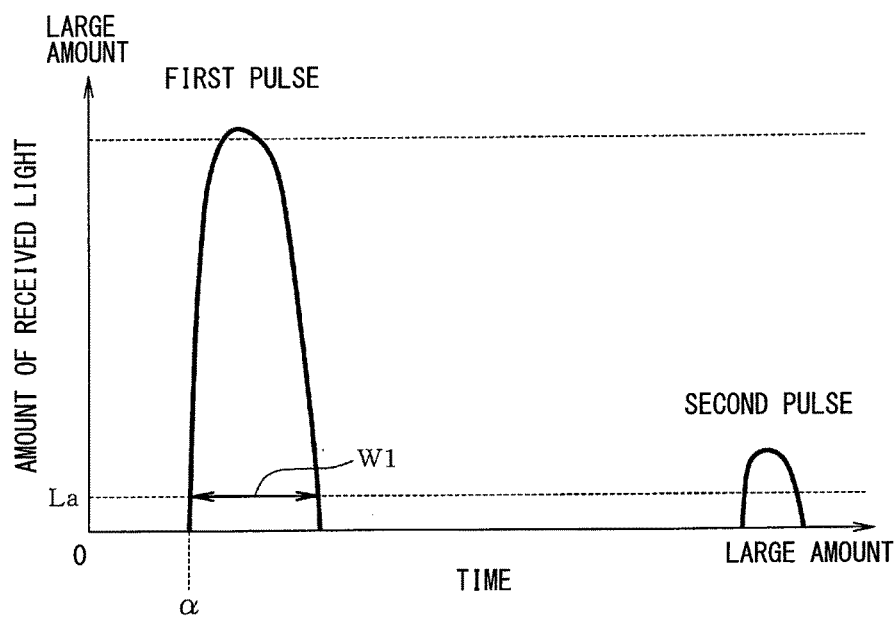
FIG. 8 is an illustration diagram of a pulse in the foreign matter deposit state in the one embodiment of the present disclosure.

When the foreign matter deposits on the front screen 12, the foreign matter detector 42 detects the first pulse and the second pulse, as shown in FIG. 7. The first pulse and the second pulse are detected for each of the plural scan areas. When the foreign matter deposits on the front screen 12, in the scan area corresponding to a foreign matter deposit position of the front screen 12, the first pulse is detected at the lapse time that corresponds to a distance α to the front screen 12 as shown in FIG. 8. The foreign matter detector 42 determines whether the first pulse is greater than a lower limit amount La of the received light. This lower limit amount La is set up to distinguish the electrical signal outputted from the receiver 22 from the noise. That is, the foreign matter detector 42 determines that the first pulse is a noise, when the amount of the received light in the first pulse is equal to or smaller than the lower limit amount La. The foreign matter detector 42 obtains a pulse width W1 of the first pulse, when the amount of the received light in the first pulse is greater than the lower limit amount La. This pulse width W1 is a timewise width of the first pulse when the received light has at least the lower limit amount La.

As shown in FIG. 5, the first pulse is generated by the internal reflection R. The pulse width of the first pulse by the internal reflection R is smaller than a pulse width W1 of the first pulse generated by the foreign matter deposited on the front screen 12. Therefore, the foreign matter detector 42 determines whether the first pulse is caused by the foreign matter deposited on the front screen 12, or is caused by the internal reflection R by obtaining the pulse width W1 of the first pulse.

The foreign matter detector 42 determines whether the pulse width W1 exceeds a determination value β by obtaining the pulse width W1 of the first pulse. Here, the determination value β may be defined as a threshold of foreign matter deposition at each angle. The foreign matter detector 42 determines that the foreign matter is deposited on the front screen 12 when the pulse width W1 exceeds the determination value β. After such determination, the foreign matter detector 42 memorizes the scan area(s) determined as having the foreign matter deposited thereon in RAM or in the not-illustrated storage medium. That is, the foreign matter detector 42 memorizes which one or more of the scan areas have the detected deposit of the foreign matter among the scan areas covering the front screen 12.

(Foreign Matter Deposit Final Determination)

When the foreign matter detector 42 determines that the foreign matter is deposited on the front screen 12 and calculates a ratio A of the scan areas having the deposit, the detector 42 performs a foreign matter deposit final determination that finally determines whether the foreign matter deposits on the front screen 12. Depending on the installation position, the optical distance sensor 10 may have various deposit conditions (i.e., may have different degrees of how dirty the front screen 12 becomes).

For example, the optical distance sensor 10 installed in an outdoor position becomes dirty more easily than the optical distance sensor 10 installed in an indoor position. Further, the two different foreign matter detection criteria may be required for a very precise detection and for a more lax detection (e.g., when a very small foreign matter needs to be detected and when a small foreign matter needs not be detected). Further, the deposited foreign matter may be removed by rain, wind, etc. Therefore, when a deposit on the front screen 12 is detected, the foreign matter detector 42 performs a process whether the deposit on the front screen 12 is finally determined as a foreign matter.

The foreign matter detector 42 calculates how much percentage of the entire front screen 12 is occupied by the detected foreign matter. In other words, the ratio A is calculated as a division of the foreign matter detected scan areas by the number of scan areas covering the entire front screen 12. The foreign matter detector 42 determines that the foreign matter is "found" (i.e., deposited) on the front screen 12, when (i) the foreign matter is detected on the screen 12, and (ii) the ratio A exceeds a preset ratio γ continuously for a first preset time T1.

On the other hand, even after the determination that the foreign matter is detected on the screen 12, when the ratio A is equal to or below a preset ratio δ continuously for a second preset time T2, the foreign matter detector 42 determines that the foreign matter is "not found" (i.e., not deposited), on the front screen 12 (i.e., the front screen 12 is without foreign matter deposition). For example, in case that the optical distance sensor 10 is installed in the outdoor position, the foreign matter deposited on the front screen 12 may be removed by the rain, wind, etc. Even when the optical distance sensor 10 is installed in the indoor position, the foreign matter deposited on the front screen 12 is removed by an air blow, washing, etc.

Therefore, the foreign matter detector 42 is configured to determine that the foreign matter is "found," when the detected foreign matter is continuously detected for the first preset time T1. Even after the foreign matter is detected or is "found", if no foreign matter is detected continuously for the second preset time T2, the foreign matter detector 42 determines that no foreign matter is found. Thereby, whether the foreign matter deposits on the screen 12 or not is determined according to the installation position/environment.

The preset ratio γ, the preset ratio δ, and the first and second preset times T1, T2 may be set according to the installation position of the optical distance sensor 10 and the like (e.g., arbitrarily determined according to various conditions). The preset ratio γ and the preset ratio δ may be set up, for example, as a percentage (%). For example, preset ratio γ may be a threshold of how much percentage of slices between scan start position P1 and scan end position P2 has foreign matter. Also, preset ratio δ may be a threshold of releasing the foreign matter deposition determination.

In other words, the determination value β, the preset ratio γ, and the preset ratio δ may vary depending on a hardware specification.

Figure 9:
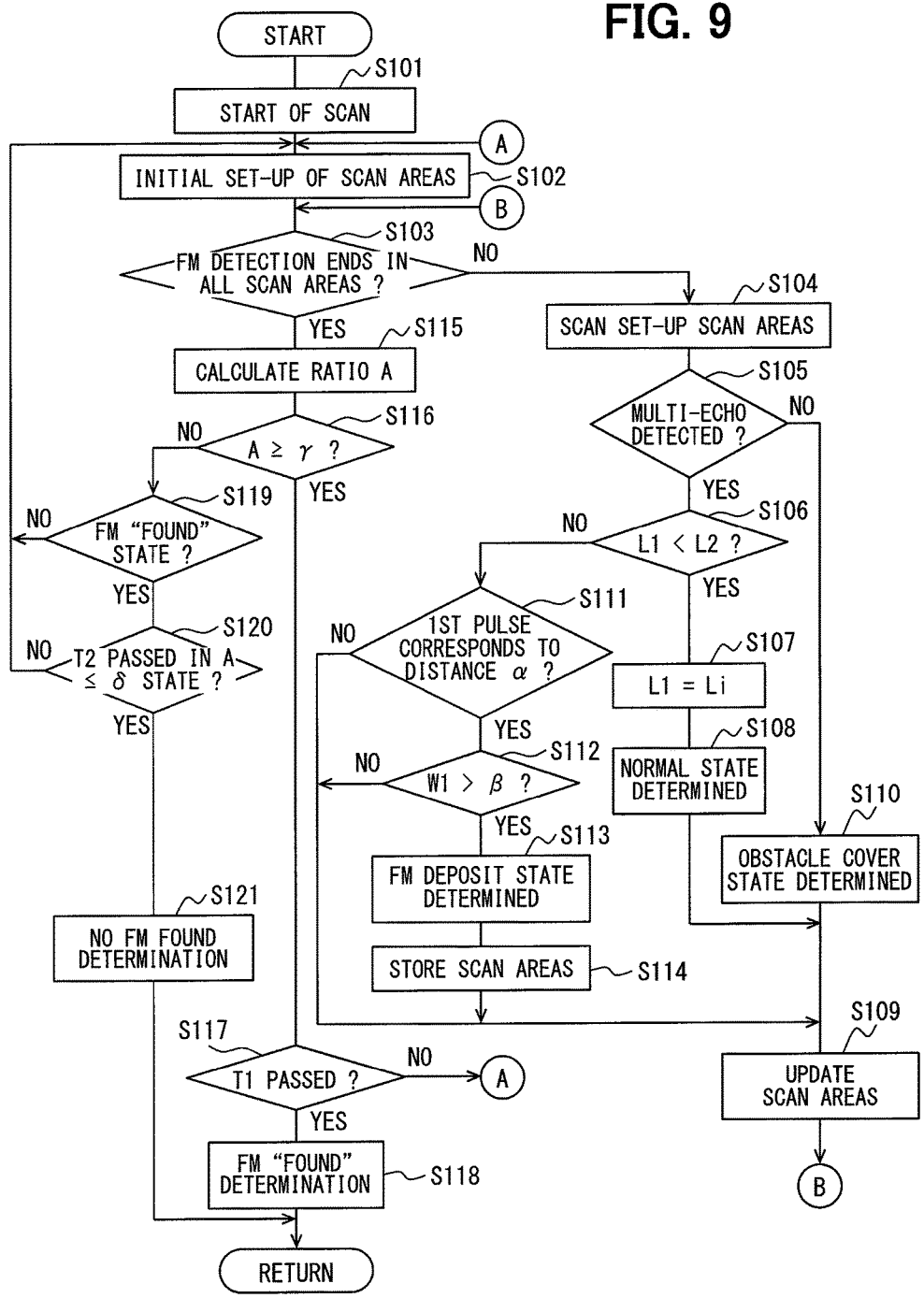
FIG. 9 is a flowchart of a process of the optical distance sensor in the one embodiment of the present disclosure.

Next, a flowchart of the process performed by the optical distance sensor 10 having the above-mentioned configuration is described based on FIG. 9.

The foreign matter detector 42 performs an initial setting of the scan area (S102), when the scan is started (S101). That is, the foreign matter detector 42 sets up the scan start position P1 as initialization of the scan area for the scanning. Then, the foreign matter detector 42 determines whether detection of the foreign matter deposit on the front screen 12 is finished for all scan areas (S103). That is, the foreign matter detector 42 determines whether detection of foreign matter deposit is completed about each of the scan areas that are set up with the equal angle intervals from the scan start position P1 to the scan end position P2.

When it is determined that detection of the foreign matter deposit is not finished for all scan areas (S103:No), the set-up scan areas are scanned (S104). That is, the foreign matter detector 42 performs detection of the foreign matter deposit in the set-up scan areas. When the foreign matter detector 42 shifts to detection of the foreign matter deposit in the set-up scan areas in S104, the detector 42 determines whether a multi-echo is detected (S105). That is, the foreign matter detector 42 determines whether the amount of the received light by the receiver 22 is in a multi-echo state (i.e., the received light includes the first pulse and the second pulse) as shown in FIGS. 4, 5, and 7.

When it is determined that the multi-echo is detected (S105:Yes), the foreign matter detector 42 determines whether the second light amount L2 of the second pulse is greater than the first light amount L1 of the first pulse (S106). When the foreign matter detector 42 determines that L2 is greater than L1 as shown in FIG. 5 (S106:Yes), the foreign matter detector 42 sets the first light amount L1 to the internal light amount Li of the internal reflection (S107). Then, it is determined by the foreign matter detector 42 that the optical distance sensor 10 is in a normal state (i.e., no foreign matter deposits on the front screen 12) (S108). When determining that the sensor 10 is in the normal state, the foreign matter detector 42 updates the scan areas (S109), and the process returns to S103. That is, the foreign matter detector 42 updates the scan areas, and uses the updated scan areas for the next scanning (i.e., in the next round of scanning from the position P1 to the position P2).

On the other hand, when the foreign matter detector 42 determines that the multi-echo is not detected (S105:No), it is determined that the sensor 10 is in the obstacle cover state (S110). That is, when the multi-echo is not detected, the pulse in the received light received by the receiver 22 has only one pulse as shown in FIG. 6. For example, when an obstacle covers an outside of the front screen 12, the light emitted from the emitter 21 is reflected by the obstacle covering the front screen 12. Therefore, the receiver 22 receives the light reflected by this obstacle covering the front screen 12, and the pulse in the received light is only one. In such a situation, the amount of the received light received by the receiver 22 increases to the excess light amount Lo that is greater than the first light amount L1 in the normal state. The foreign matter detector 42 updates the scan areas (S109) upon determining that the sensor 10 is in the obstacle cover state, and the process returns to S103.

When it is determined that the second light amount L2 is not greater than the first light amount L1 in S106 (S106:No), the foreign matter detector 42 then determines whether the first pulse corresponds to a distance α to the front screen 12 (S111). That is, the foreign matter detector 42 determines whether the first pulse in the multi-echo is a reflection from the front screen, 12 which is at the distance α as shown in FIG. 8.

When it is determined that the first pulse corresponds to the distance α (S111:Yes), the foreign matter detector 42 determines whether the pulse width W1 of the first pulse in the first pulse having the lower limit amount La of the received light exceeds a determination value β (S112).

On the other hand, when it is determined that the first pulse does not corresponds to the distance α (S111:No), the foreign matter detector 42 updates the scan areas (S109), and the process returns to S103. Note that, when the first pulse does not correspond to the distance α, such a situation means that the light emitted from the emitter 21 enters into the receiver 22 before reaching the front screen 12. Therefore, the foreign matter detector 42 excludes/disregards a pulse corresponding to the amount of the received light indicating a position closer than the distance α.

When it is determined that the pulse width W1 of the first pulse exceeds the determination value β (S112:Yes), the foreign matter detector 42 determines that the sensor 10 is in the foreign matter deposit state (S113). The foreign matter detector 42 stores the scan areas that are determined as being in the foreign matter deposit state in RAM of the controller or the like, for example (S114). That is, when the pulse width W1 of the first pulse exceeds the determination value β, the foreign matter detector 42 determines that the foreign matter is deposited on the scan area of the front screen 12 currently scanned, and memorizes such a scan area. After storing the scan area, the foreign matter detector 42 updates the scan areas (S109), and the process returns to S103.

On the other hand, when the foreign matter detector 42 determines that the pulse width W1 of the first pulse does not exceed the determination value β (S112:No), the foreign matter detector 42 updates the scan areas (S109), the process returns to S103. Note that, when the pulse width W1 of the first pulse does not exceed the determination value β, such a situation means that the pulse of the received light is a noise, for example.

The foreign matter detector 42 determines in S103 whether detection of the foreign matter deposit is finished in all scan areas after repeating the process of S104 to S114.

That is, the foreign matter detector 42 determines whether the scanning in all scan areas set up between the scan start position P1 and the scan end position P2 is now complete.

When it is determined that detection of the foreign matter deposit has finished for all scan areas (S103:Yes), the foreign matter detector 42 calculates the ratio A of the scan areas having the detected foreign matter (S115). That is, the foreign matter detector 42 calculates the ratio A of the scan area determined as having the foreign matter deposit in S113 against the entire scan area.

After calculating the ratio A in S115, the foreign matter detector 42 determines that the calculated ratio A is equal to or greater than the preset ratio γ (S116). When it is determined that the ratio A is equal to or greater than the preset ratio γ (S116:Yes), the foreign matter detector 42 determines whether the first preset time T1 has passed (S117). When it is determined that, after determining that the ratio A is equal to or greater than the preset ratio γ, the first preset time T1 has passed (S117:Yes), the foreign matter detector 42 determines that the foreign matter is found (i.e., is deposited) on the front screen 12 (S118). That is, when the ratio A of the scan areas determined to be having the foreign matter deposit is equal to or greater than the preset ratio γ continuously for more than the first preset time T1, the foreign matter detector 42 determines that the foreign matter is "found" on the front screen 12.

On the other hand, when it is determined that the first preset time T1 has not passed in S117 (i.e., after the determination that the ratio A is equal to or greater than the preset ratio γ) (S117:No), the process returns to S102. Then, the foreign matter detector 42 repeats the process of S103 and thereafter for the scanning from the scan start position P1.

When it is determined in S116 that the ratio A of the scan area is not equal to or greater than the preset ratio γ (S116:No), the foreign matter detector 42 determines whether it is in a state that the foreign matter is "found" (S119). That is, when the ratio A of the scan areas is not equal to or greater than the preset ratio γ, the foreign matter detector 42 determines whether an immediate-before round of the process has determined in S118 that the foreign matter is "found".

When it is determined that the immediate-before round of the process has determined that the foreign matter is "found" (S119:Yes), the foreign matter detector 42 determines whether the second preset time T2 has passed in a state that the ratio A is equal to or less than the preset ratio δ (S120).

When it is determined that the second preset time T2 has passed in the state that the ratio A is equal to or less than the preset ratio δ (S120:Yes), the foreign matter detector 42 determines that the front screen 12 does not have the foreign matter deposit (S121). That is, when it is determined by the foreign matter detector 42 that, after the determination that the foreign matter is "found", the second preset time T2 has passed in the state that the ratio A is equal to or less than the preset ratio δ, it should be determined that the foreign matter deposited on the front screen 12 has disappeared.

The foreign matter deposited on the optical distance sensor 10 may be removed by the rain, wind, etc., for example. Therefore, the foreign matter on the front screen 12 having been "found" once may later disappear. Thus, even after the determination that the foreign matter is "found" on the front screen 12, the foreign matter detector 42 determines that the foreign matter is "gone" if the foreign matter is not detected under a certain condition.

The process performed by the foreign matter detector 42 returns to S102, when, in S119, it is determined in the immediate-before round of the process that the foreign matter is not determined as being "found" or when, in S120, it is determined that the second preset time T2 has not passed. Then, the foreign matter detector 42 repeats the process of S103 and thereafter for the scanning from the scan start position P1.

According to the one embodiment described above, the foreign matter detector 42 detects the foreign matter deposited on the front screen 12 by calculating the difference of the amounts of the received light between the first pulse corresponding to the internal reflection R and the second pulse corresponding to a reflection by the detection object 30, taking advantage of the coaxial optical system for the distance measurement. That is, in the one embodiment of the present disclosure, the internal reflection R conventionally shunned and eliminated in the sensor device is positively utilized. In other words, the optical distance sensor 10 is enabled to accurately detect the foreign matter for the entire surface of the front screen 12, without complicating the optical system structure and without adding extra parts.

Further, in the one embodiment, the emitter 21 emits the light to the scan areas with the equal (i.e., with consistent) angle detection intervals from the scan start position P1 to the scan end position P2. Then, the foreign matter detector 42 identifies the range of the scan areas having the foreign matter deposited thereon, when it is determined to be in the foreign matter deposit state. Thereby, the foreign matter detector 42 detects not only the position of the foreign matter deposit but also the range of the scan areas having the foreign matter (i.e., the size of the foreign matter).

The optical distance sensor 10 may have different tolerances for the foreign matter (i.e., to what extent the foreign matter is allowed to deposit), depending on the installation position or on the other requirements etc. According to the one embodiment, by detecting the range of the scan areas having the foreign matter deposit on the front screen 12, a clue for a determination of whether such foreign matter is tolerable or not is provided. In other words, detection of the foreign matter is performable with high accuracy according to the condition of the foreign matter.

According to the one embodiment, when the foreign matter detector 42 continuously detects the foreign matter for the first preset time T1, the foreign matter detector 42 determines that the foreign matter is found.

On the other hand, when the foreign matter detector 42 does not detect the foreign matter continuously for the second preset time T2 after the detection of the foreign matter deposition, the foreign matter detector 42 determines that no foreign matter deposits on the front screen.

When the optical the distance sensor 10 is installed in the outdoor environment, the foreign matter deposited on the front screen 12 may be removed by rain, wind or the like.

Therefore, in the one embodiment, even after the determination of the foreign matter deposition, the absence of the foreign matter continuously for the second preset time T2 is assumed as a removal of the foreign matter, thereby determining that the foreign matter is gone (i.e., is not deposited any more).

Therefore, accurate detection of the foreign matter is performed according to the use environment of the optical distance sensor 10.

According to the one embodiment, the foreign matter detector 42 determines the amount of the received light based on the intensity of the received light received by the receiver 22. The receiver 22 outputs the electrical signal (e.g., voltage), according to the intensity of the received light. The foreign matter detector 42 uses the output of the electrical signal from the receiver 22 according to the intensity of the received light as the amount of the received light, as it is (i.e., without change). Therefore, the amount of the received light is converted to a simple magnitude of the signal value, thereby simplifying an internal processing of the sensor 10. That is, even when the resolution of the scanning is high (i.e., even when the equal angle intervals dividing the scan surface Sa are very small) and defining many scan areas, the internal processing is quickly performable.

Other Embodiments

The present disclosure described above is not limited to the above-mentioned embodiment, and is applicable to the various other embodiments and modifications as long as it pertains to the scope of the present disclosure.

According to the one above-mentioned embodiment, the intensity of the received light by the receiver 22 (i.e., the electrical signal outputted from the receiver 22), is used by the foreign matter detector 42 as an amount of the received light as it is (i.e., without change).

However, the foreign matter detector 42 may interpret the pulse width of the first pulse and the second pulse received by the receiver 22 as the amount of the received light.

When the light reflected either by the detection object 30 or the foreign matter deposited on the front screen 12 becomes strong or intense, the pulse width of the electrical signal outputted from the receiver 22 increases. That is, the timewise width of the pulse from the receiver 22 between an output start timing of the pulse and an output end/stop timing of the pulse increases.

That is, the pulse width is correlated with the amount of the received light. The foreign matter detector 42 uses this timewise width of the pulse as the amount of the received light. Thereby, the amount of the received light is converted to the time between ON and OFF of the signal, and the internal process of the sensor 10 is simplified. Thus, a quick processing is enabled even when scanning resolution is high.

The foreign matter detector 42 may interpret an energy of the light received by the receiver 22 as the amount of the received light. The energy of the light corresponds to the integration value of the first pulse or the second pulse. In other words, the energy of the light is calculated as a time-integration of the first/second pulse based on the output of the electrical signal according to the intensity of the received light by the receiver 22. Therefore, the amount of the received light is converted to a simple magnitude of the integration value. When the integration values are calculated, even though the calculation time for integration increases, the measurement/calculation accuracy of the amount of the received light is improved, thereby enabling an accurate detection of the foreign matter.

Such changes, modifications, and summarized schemes are to be understood as being within the scope of the present disclosure as defined by appended claims.

What is claimed is:

1. An optical distance sensor including an optical system having a coaxial optical path on which a light emitter for emitting light that is reflected by a detection object, and a light receiver for receiving a reflected light are coaxially placed, together with a front screen placed on the coaxial optical path, the optical distance sensor comprising:
    a time counter counting time between emission of the light from the light emitter and reception of the light by the light receiver as counted time; and
    an foreign matter (FM) detector detecting a deposition of foreign matter on the front screen based on a relationship between the counted time and an amount of the light received by the light receiver, wherein
    the FM detector detects a first pulse as the light not passing through the front screen and a second pulse as the light reflected back from the detection object,
    (A) the FM detector determines that (i) a first light amount of the first pulse is an internal reflection amount of the light reflected by an inner surface of the front screen, and (ii) the front screen is in a normal state without foreign matter deposited on the front screen, when a second light amount of the second pulse is greater than the first light amount of the first pulse,
    (B) the FM detector determines an obstacle cover state that the front screen is covered by an obstacle that is wider than a front cover, when the first light amount of the first pulse is detected to be substantially equal to an excess light amount, without detection of the second pulse, and
    (C) the FM detector determines a foreign matter deposit state of having foreign matter on an outside of the front screen, when (i) the first light amount of the light of the first pulse is greater than the internal reflection light amount and is smaller than the excess light amount, and (ii) the second light amount of the second pulse is smaller than the second light amount detected during the normal state.

2. The optical distance sensor of claim 1, wherein the light emitter emits the light for each of scan areas that are positioned between a scan start position and a scan end position at constant intervals, and
in the foreign matter deposit state, the FM detector detects an angle of the foreign matter deposition based on a range of the scan areas from which the light receiver receives the first pulse having (i) a lower limit amount that is set for noise filtering and (ii) a pulse width greater than a determination value.

3. The optical distance sensor of claim 2, wherein
(A) the FM detector determines that the foreign matter deposition exists on the front screen, when a ratio of the scan areas in the foreign matter deposit state against an entire range of the scan areas is equal to or greater than a preset ratio continuously for a first preset time, and
(B) after a determination of deposition of the foreign matter on the front screen, the FM detector determines that the front screen is without foreign matter deposition, when the ratio of the scan areas in the foreign matter deposit state against the entire range of the scan areas is equal to or smaller than a preset ratio continuously for a second preset time.

4. The optical distance sensor of claim 1, wherein the FM detector determines the amount of the received light based on an intensity of the received light received by the light receiver.

5. The optical distance sensor of claim 1, wherein the FM detector determines the amount of the received light based on a timewise width of the first pulse or the second pulse of the received light received by the light receiver.

6. The optical distance sensor of claim 1, wherein the FM detector determines the amount of the received light based on an energy of the received light received by the light receiver.

7. The optical distance sensor of claim 1, wherein during the obstacle covered state, the first light amount is greater than the first light amount detected during the normal state.

8. The optical distance sensor of claim 1, wherein during the foreign matter deposit state, the first light amount is greater than the second light amount.

* * * * *